(12) United States Patent
Monge Vega et al.

(10) Patent No.: US 6,271,247 B1
(45) Date of Patent: Aug. 7, 2001

(54) HYDRAZIDE COMPOUNDS

(75) Inventors: Antonio Monge Vega, Cizur Menor; Ignacio Aldana Moraza, Pamplona, both of (ES); Daniel-Henri Caignard, Le Pecq (FR); Jacques Duhault, Croissy sur Seine (FR); Jean Boutin, Suresnes (FR); Odile Dellazuana, Romainville (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/602,538

(22) Filed: Jun. 23, 2000

Related U.S. Application Data

(62) Division of application No. 09/464,182, filed on Dec. 16, 1999, now Pat. No. 6,172,108.

(30) Foreign Application Priority Data

Dec. 17, 1998 (ES) .................................... 9802626

(51) Int. Cl.[7] ........................ A61K 31/15; C07C 243/28; C07C 243/30; C07C 243/32; C07C 243/34
(52) U.S. Cl. ...................... 514/356; 514/419; 514/423; 514/448; 546/279.1; 546/316; 548/492; 548/537; 549/72
(58) Field of Search ................... 514/256, 311, 514/326, 355, 356, 419, 423, 448; 544/335; 546/172, 279.1, 316; 548/492, 537; 549/72

(56) References Cited

U.S. PATENT DOCUMENTS 5,235,058 * 8/1993 Sato et al. ...................... 546/279

OTHER PUBLICATIONS

Braichenko et al., N–aryl–beta–amino acid. III N–aryl–sulfonyl–beta–alanine hydrazides Khim. –Farm. Zh. 6(8), pp. 6–8, (1972).*

* cited by examiner

Primary Examiner—Mukund J. Shah
Assistant Examiner—Deepak R. Rao
(74) Attorney, Agent, or Firm—The Firm of Hueschen and Sage; G. Patrick Sage

(57) ABSTRACT

Compounds of formula (I):

$$R-NH-A-CO-NH-NH-(W)_n-Z \qquad (I)$$

wherein:

n is 0 or 1,

W represents —CO— or $S(O)_r$ wherein r is 0, 1 or 2,

Z represents a group selected from aryl, arylalkyl, heteroaryl and heteroarylalkyl, each optionally substituted, R represents a grouping selected from:
$Z_1$—T—CO—, $Z_1$—O—T—CO—, $Z_1$—T—O—CO—, $Z_1$—T—$S(O)_q$—
wherein $Z_1$, T and q are as defined in the description, A represents alkylene, alkenylene or alkynylene each having from 3 to 8 carbon atoms, alkylenecycloalkylene, cycloalkylenealkylene, alkylenecycloalkylenealkylene, alkylenearylene, arylenealkylene, alkylenearylenealkylene a grouping

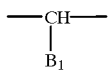

wherein $B_1$ is as defined in the description, or A forms with the adjacent nitrogen atom a grouping

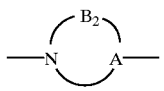

as defined in the description.

Medicinal products containing the same are useful as Neuropeptide Y receptors ligands.

18 Claims, No Drawings

HYDRAZIDE COMPOUNDS

The present application is a division of our prior-filed application Ser. No. 09/464,182, filed Dec. 16, 1999, now U.S. Pat. No. 6,172,108, issued Jan. 9, 2001.

The present invention relates to new hydrazide compounds.

DESCRIPTION OF THE PRIOR ART

Hydrazide compounds have been described in the literature (J. Org. Chem., 1971, 36, 1580) although no pharmacological property has been mentioned. Other compounds of related structure are used in the composition of photographic films (JP 02008833), or have been used in the formation of polymers that are used to prepare semipermeable membranes (J. Appl. Polym. Sci., 1992, 44, 1383).

The compounds of the present invention have a novel structure which imparts to them great affinity for neuropeptide Y receptors.

Ligands of those receptors have been described recently. By way of example, there may be mentioned cyclic peptide compounds (WO 9400486), amino acid compounds of arginine (WO 9417035), or non-peptide compounds having a guanidine group (EP 448765, J. Med. Chem., 1994, 37, 2242).

BACKGROUND OF THE INVENTION

Neuropeptide Y (NPY) is a peptide of 36 amino acids, related to the peptide YY (PYY) and to pancreatic polypeptides (PP). Originally isolated from pig brain (Proc. Natl. Acad. Sci., 1982, 79, 5485), NPY is widely distributed in mammals at the level of the central and peripheral nervous systems. This neurotransmitter is present in high concentrations in nerve fibres of the brain, but also of the heart, the sympathetic ganglia, blood vessels and smooth muscles of the vas deferens and of the gastrointestinal tract. It is responsible for various physiological effects which are exerted via the intermediary of specific receptors (Y). The latter form a heterogeneous group, 6 sub-types of which have been identified to date: $Y_1$ to $Y_6$ (Pharmacological Reviews, 1998, 50, 143). NPY is involved in eating behaviour by strongly stimulating food intake (Proc. Natl. Acad. Sci., 1985, 82, 3940) or by exerting a regulatory role on the HPA (hypothalamic-pituitary-adrenal) axis (J. of Neuroendocrinol., 1995, 7, 273). It also exhibits anxiolytic and sedative properties (Neuropsycho-pharmacology, 1993, 8, 357), a strong vasoconstrictive ability (Eur. J. Pharmacol., 1984, 85, 519) which induces an increase in blood pressure, and also has an effect on the circadian rhythm (Neuroscience and biobehavioral reviews, 1995, 19, 349). In addition to the fact that the compounds of the invention are new, they have a structure which imparts to them great affinity for NPY receptors. It will thus be possible to use them in the treatment of pathologies in which an NPY receptor ligand is necessary, especially in the treatment of pathologies associated with eating behaviour disorders or energy balance disorders, such as diabetes, obesity, bulimia, anorexia nervosa, and also in the treatment of arterial hypertension, anxiety, depression, epilepsy, sexual dysfunctions and sleep disorders.

DETAILED DESCRIPTION OF THE INVENTION

The present invention relates to compounds of formula (I):

$$R\text{—}NH\text{—}A\text{—}CO\text{—}NH\text{—}NH\text{—}(W)_{n}\text{—}Z \qquad (I)$$

wherein:
n is 0 or 1,
W represents a —CO— group or an S(O)$_r$ group wherein r is 0, 1 or 2,
Z represents a group selected from optionally substituted aryl, optionally substituted arylalkyl, optionally substituted heteroaryl and optionally substituted heteroarylalkyl,
R represents a group selected from
$Z_1$—T—CO—
$Z_1$—O—T—CO—
$Z_1$—T—O—CO—
$Z_1$—T—S(O)$_q$—
wherein:
$Z_1$ represents an optionally substituted aryl, optionally substituted arylalkyl, optionally substituted heteroaryl or optionally substituted heteroarylalkyl group,
T represents a σ bond or an alkylene, alkenylene or alkynylene group,
q represents an integer 0, 1 or 2,
A represents a linear or branched alkylene group having from 3 to 8 carbon atoms, a linear or branched alkenylene group having from 3 to 8 carbon atoms, a linear or branched alkynylene group having from 3 to 8 carbon atoms, an alkylenecycloalkylene group, a cycloalkylenealkylene group, an alkylenecycloalkylenealkylene group, an alkylenearylene group, an arylenealkylene group, an alkylenearylenealkylene group, a grouping

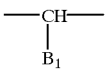

wherein $B_1$ represents an optionally substituted aryl, optionally substituted arylalkyl, optionally substituted heteroaryl or optionally substituted heteroarylalkyl group, or A forms with the nitrogen atom a grouping

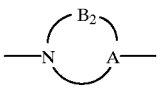

wherein $B_2$ represents a saturated or unsaturated mono- or bi-cyclic system having from 5 to 11 ring members, optionally containing from 1 to 3 additional hetero atoms selected from nitrogen, oxygen and sulphur,
with the proviso that when simultaneously n is 0, A represents a grouping

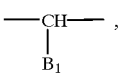

$B_1$ being
a benzyl group, and Z represents an optionally substituted phenyl group, then R is other than a benzoyl group,
their enantiomers, diastereoisomers, and addition salts thereof with a pharmaceutically acceptable acid or base,
it being understood that:
the term "alkyl" denotes a linear or branched group having from 1 to 6 carbon atoms, the term "alkylene" denotes a linear or branched bivalent radical containing from 1 to 6 carbon atoms, unless indicated otherwise, the term "alkenylene" denotes a linear or branched bivalent radical containing from 2 to 6 carbon atoms and from 1 to 3 double bonds, unless indicated otherwise, the term "alkynylene" denotes a linear or branched bivalent radical containing from 2 to 6 carbon atoms and from 1 to 3 triple bonds, unless indicated otherwise, the term "aryl" denotes a phenyl, naphthyl, dihydronaphthyl or tetrahydronaphthyl group, and the term "arylene" denotes a bivalent radical of the same type, the term "heteroaryl" denotes an unsaturated or partially unsaturated mono- or bi-cyclic group having from 5 to 11 ring members, containing from 1 to 4 hetero atoms selected from nitrogen, oxygen and sulphur, the term "alkylenecycloalkylene" represents a grouping $-A_1-A_2-$, the term "cycloalkylene-alkylene" represents a grouping $-A_2-A_1-$, and the term "alkylenecycloalkylenealkylene" represents a grouping $-A_1-A_2-A_1-$, the term "alkylenearylene" represents a grouping $-A_1-A_3-$, the term "arylenealkylene" represents a grouping $-A_3-A_1-$, the term "alkylenearylenealkylene" represents a grouping $-A_1-A_3-A_1-$, wherein $A_1$ is an alkylene group as defined hereinbefore, $A_2$ is a $(C_4-C_8)$cycloalkylene group, and $A_3$ is an arylene group as defined hereinbefore, the expression "optionally substituted" applied to the terms "aryl", "arylalkyl", "heteroaryl" and "heteroarylalkyl" indicates that those groups are substituted on their cyclic moiety by from 1 to 5 identical or different substituents selected from linear or branched $(C_1-C_6)$alkyl, linear or branched $(C_1-C_6)$alkoxy, halogen, hydroxy, perhalo-$(C_1-C_6)$alkyl in which the alkyl moiety is linear or branched, nitro, linear or branched $(C_1-C_6)$acyl, linear or branched $(C_1-C_6)$alkylsulphonyl, and amino (amino optionally being substituted by one or two linear or branched $(C_1-C_6)$alkyl and/or linear or branched $(C_1-C_6)$acyl groups).

Among the pharmaceutically acceptable acids, there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases, there may be mentioned by way of non-limiting example sodium hydroxide, potassium hydroxide, triethylamine, tert-butylamine, etc.

Advantageously, the invention relates to compounds of formula (I) wherein R represents a grouping $Z_1-T-CO$, $Z_1$ preferably being an optionally substituted aryl group, and T preferably being an alkylene group or a bond.

Another advantageous aspect of the invention relates to compounds of formula (I) wherein R represents a grouping $Z_1-O-T-CO$, $Z_1$ preferably being an optionally substituted aryl group, and T preferably being an alkylene group or a bond.

Another advantageous aspect of the invention relates to compounds of formula (I) wherein R represents a grouping $Z_1-T-O-CO$, $Z_1$ preferably being an optionally substituted aryl group, and T preferably being an alkylene group or a bond.

Another advantageous aspect of the invention relates to compounds of formula (I) wherein R represents a grouping $Z_1-T-S(O)_q-$, $Z_1$ preferably being an optionally substituted aryl group, and T preferably being an alkylene group or a bond, and q preferably being 2.

The preferred aryl group are phenyl or naphthyl.

Preferred compounds of the invention are those wherein W represents a $-CO-$ group.

Other preferred compounds of the invention are those wherein W represents an $SO_2$ group.

In the preferred compounds of the invention, Z represents a group selected from optionally substituted aryl and optionally substituted heteroaryl.

Preferred compounds of the invention are those wherein A represents a grouping

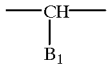

wherein $B_1$ is an optionally substituted arylalkyl group (for example a benzyl or tolylmethyl group).

Other preferred compounds of the invention are those wherein A represents an alkylene-cycloalkylene group (for example methylenecyclohexylene).

Other preferred compounds of the invention are those wherein A represents an alkylenearylene group (for example methylenephenylene).

In the compounds of the invention, the cyclic groupings

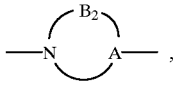

are advantageously selected from pyrrolidine, perhydroindole and piperidine groups.

In an especially advantageous manner, the invention relates to compounds of formula (I) wherein W represents a $-CO-$ group, Z represents a group selected from optionally substituted aryl and optionally substituted heteroaryl, R represents a grouping selected from $Z_1-T-CO-$, $Z_1-O-T-CO-$, $Z_1-T-O-CO-$ and $Z_1-T-S(O)_q-$ wherein $Z_1$ is preferably an optionally substituted aryl or optionally substituted heteroaryl group, T represents an alkylene group (for example methylene), and q is 2, and A represents an alkylene-cycloalkylene group, a grouping

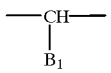

wherein $B_1$ is an optionally substituted arylalkyl group, or A forms with the adjacent nitrogen atom a pyrrolidine, perhydroindole or piperidine group.

Among the preferred compounds of the invention, there may be mentioned:
- N2-({4-[(2-benzoylhydrazino)carbonyl] cyclohexyl}methyl)-2-naphthalenesulphonamide
- N1-({4-[(2-benzoylhydrazino)carbonyl] cyclohexyl}methyl)-1-(2-nitrobenzene)-sulphonamide
- N1-[1-benzyl-2-oxo-2-(2-phenylhydrazino)ethyl]-1-(4-chlorobenzene)sulphonamide The present invention relates also to a process for the preparation of compounds of formula (I), characterised in that there is used as starting material a compound of formula (II):

$$H_2N-A-COOH \qquad (II)$$

wherein A is as defined for formula (1),
which is condensed in a basic medium with a halogen compound of formula (III):

R—Cl    (III)

wherein R is as defined for formula (I),
to yield a compound of formula (IV):

R—NH—A—COOH    (IV)

wherein R and A are as defined hereinbefore,
which compound (IV) is condensed, in the presence of a coupling agent, with a monosubstituted hydrazine of formula (V), H$_2$N—NH—(W)$_n$—Z    (V)

wherein n, W and Z are as defined for formula (I),
to yield compounds of formula (I):

R—NH—A—CO—NH—NH—(W)$_n$—Z    (I)

wherein R, A, n, W and Z are as defined hereinbefore,
which compound of formula (I):
may be purified, if necessary, according to a conventional purification technique,
is separated, where appropriate, into its isomers according to a conventional separation technique,
is converted, if desired, into an addition salt thereof with a pharmaceutically acceptable acid or base.

The present invention relates also to pharmaceutical compositions comprising as active ingredient at least one compound of formula (I), on its own or in combination with one or more inert non-toxic excipients or carriers.

Among the pharmaceutical compositions according to the invention, there may be mentioned more especially those that are suitable for oral, parenteral or nasal administration, tablets or dragées, sublingual tablets, gelatin capsules, lozenges, suppositories, creams, ointments, dermal gels, etc.

The useful dosage varies according to the age and weight of the patient, the nature and severity of the disorder and the route of administration, which may be oral, nasal, rectal or parenteral. Generally the unit dose ranges from 0.05 to 500 mg for a treatment in from 1 to 3 administrations per 24 hours.

The following Examples illustrate the invention but do not limit it in any way. The structures of the compounds described were confirmed by the usual spectroscopic techniques.

The starting materials used are known products or are prepared according to known procedures.

EXAMPLE 1

Benzyl N-[1-benzyl-2-oxo-2-(2-phenylhydrazino)ethyl]carbamate

Step a: 2-Benzyloxycarbonylamino-3-phenylpropanoic acid 82 mmol (13.9 g) of benzyl chloroformate and 20 ml of 4M aqueous sodium hydroxide are added over a period of 30 minutes to a solution, cooled to 0° C., of 80 mmol (13.2 g) of phenylalanine in 20 ml of 4M aqueous sodium hydroxide. The solution returns to room temperature during a period of 1 hour. The reaction mixture is extracted with ether. The aqueous phase is rendered acidic to pH=2 with a dilute hydrochloric acid solution. The precipitate that forms is filtered off and washed to yield the expected compound.

Step b: Benzyl N-[1-benzyl-2-oxo-2-(2-phenylhydrazino)ethyl]carbamate 3.25 mmol (0.63 g) of EDC are added to a solution, cooled to 0° C., of 2.85 mmol (0.8 g) of the compound described in the preceding Step and 3.25 mmol (0.43 g) of HOBT in 20 ml of dichloromethane. The reaction mixture is stirred at 0° C. for 1 hour and then 3.25 mmol (0.32 ml) of phenylhydrazine are added. The reaction mixture is stirred at 0° C. for 1 hour, and then at room temperature for 24 hours. The reaction mixture is filtered and the filtrate is concentrated. The resulting residue is taken up in ether (15 ml) and 10 ml of water are added. The resulting precipitate is filtered off, and washed with water and then with ether to yield the expected compound.

| Melting point: 175–177° C. | | | |
|---|---|---|---|
| Elemental microanalysis: | | | |
| | C | H | N |
| % calculated | 70.95 | 5.91 | 10.79 |
| % found | 71.27 | 5.90 | 10.71 |

EXAMPLE 2

Benzyl N-[2-(2-benzoylhydrazino)-1-benzyl-2-oxoethyl]carbamate

The expected product is obtained according to the process described in Example 1, in Step b replacing phenylhydrazine by phenylhydrazide.

| Melting point: 172–174° C. | | | |
|---|---|---|---|
| Elemental microanalysis: | | | |
| | C | H | N |
| % calculated | 69.06 | 5.52 | 10.07 |
| % found | 69.14 | 5.71 | 9.92 |

EXAMPLE 3

Benzyl N-[1-benzyl-2-oxo-2-(2-nicotinoylhydrazino)ethyl]carbamate

The expected product is obtained according to the process described in Example 1, in Step b replacing phenylhydrazine by 3-pyridinecarbohydrazide.

| Elemental microanalysis: | | | |
|---|---|---|---|
| | C | H | N |
| % calculated | 66.03 | 5.26 | 13.40 |
| % found | 66.00 | 5.72 | 13.68 |

EXAMPLE 4

Benzyl N-{1-benzyl-2-[2-(3-indolyl)acetyl]-2-oxoethyl}carbamate

The expected product is obtained according to the process described in Example 1, in Step b replacing phenylhydrazine by 3-indolylacetohydrazide.

| Elemental microanalysis: | | | |
|---|---|---|---|
| | C | H | N |
| % calculated | 68.94 | 5.53 | 11.91 |
| % found | 69.23 | 5.81 | 11.57 |

EXAMPLE 5

N1-[1-Benzyl-2-oxo-2-(2-phenylhydrazino)ethyl]-2-phenoxyacetamide

Step a: 2-[(2-Phenoxyacetyl)amino]-3-phenylpropanoic acid

A solution of 6.6 mmol (1.0 g) of phenoxyacetic acid in 15 ml of dioxane is treated with 49.3 mmol (3.6 ml) of thionyl chloride. The reaction mixture is stirred at room temperature for 2 hours and then concentrated. The residue, taken up in 10 ml of dichloromethane, and 7.9 mmol (0.3 g) of sodium hydroxide in 10 ml of water are added in succession to a solution of 7.6 mmol (1.25 g) of phenylalanine and 7.6 mmol (0.3 g) of sodium hydroxide in 10 ml of water, the temperature being maintained at 10° C. The reaction mixture is then stirred for 1 hour at room temperature. After decanting, the aqueous phase is washed with dichloromethane, and then rendered acidic to pH=2 with a dilute hydrochloric acid solution. The precipitate that forms is filtered off and recrystallised from water to yield the expected product.

Step b: N1-[1-Benzyl-2-oxo-2-(2-phenylhydrazino)ethyl]-2-phenoxyacetamide 3.7 mmol (0.71 g) of EDC are added to a solution, cooled to 0° C., of 3.35 mmol (1 g) of the compound described in the preceding Step and 3.7 mmol (0.56 g) of HOBT in 15 ml of dichloromethane. After one hour at 0° C., a solution of 3.7 mmol (0.4 g) of phenylhydrazine in 10 ml of dichloromethane is added. The reaction mixture is stirred at 0° C. for 1 hour and then at room temperature for 24 hours. The organic phase is washed with water, dried over sodium sulphate and concentrated. The resulting residue is washed in ether and then filtered to yield the expected compound.

Melting point: 172–175° C.

| Elemental microanalysis: | | | |
|---|---|---|---|
| | C | H | N |
| % calculated | 70.95 | 5.91 | 10.80 |
| % found | 70.91 | 6.06 | 10.68 |

EXAMPLE 6

N1-[2-(2-Benzoylhydrazino)-1-benzyl-2-oxoethyl]-2-phenoxyacetamide

The expected product is obtained according to the process described in Example 5, in Step b replacing phenylhydrazine by phenylhydrazide.

| Elemental microanalysis: | | | |
|---|---|---|---|
| | C | H | N |
| % calculated | 69.06 | 5.12 | 10.07 |
| % found | 68.88 | 5.52 | 9.84 |

EXAMPLE 7

N1-{1-Benzyl-2-[2-(2-indolylcarbonyl)hydrazino]-2-oxoethyl}-2-phenoxyacetamide The expected product is obtained according to the process described in Example 5, in Step b replacing phenylhydrazine by 2-indolecarbohydrazide.

| Elemental microanalysis: | | | |
|---|---|---|---|
| | C | H | N |
| % calculated | 68.42 | 5.26 | 12.28 |
| % found | 67.97 | 5.44 | 12.42 |

EXAMPLE 8

N1-[1-Benzyl-2-oxo-2-(2-nicotinoylhydrazino)ethyl]-2-phenoxyacetamide

The expected product is obtained according to the process described in Example 5, in Step b replacing phenylhydrazine by 3-pyridinecarbohydrazide.

| Elemental microanalysis: | | | |
|---|---|---|---|
| | C | H | N |
| % calculated | 64.29 | 5.36 | 12.50 |
| % found | 64.06 | 5.34 | 12.34 |

EXAMPLE 9

N2-[1-Benzyl-2-oxo-2-(2-phenylhydrazino)ethyl]-2-indolecarboxamide

Step a: 2-(2-Indolylcarbonylamino)-3-phenylpropanoic acid

The expected product is obtained according to the process described in Example 5, Step a, replacing phenoxyacetic acid by 2-indolecarboxylic acid.

Step b: N2-[1-Benzyl-2-oxo-2-(2-phenylhydrazino)ethyl]-2-indolecarboxamide

The expected product is obtained according to the process described in Example 5, Step b, using the compound described in the preceding Step as starting material.

| Elemental microanalysis: | | | |
|---|---|---|---|
| | C | H | N |
| % calculated | 72.36 | 5.53 | 14.07 |
| % found | 72.05 | 5.82 | 14.60 |

EXAMPLE 10

N2-[1-Benzyl-2-oxo-2-(2-phenylhydrazino)ethyl]-2-naphthalene-sulphonamide

Step a: 2-[(2-Naphthylsulphonyl)amino]-3-phenylpropanoic acid

A solution of 7.6 mmol (1.71 g) of 2-naphthylsulphonyl chloride in 10 ml of dichloromethane and a solution of 7.9 mmol (0.32 g) of sodium hydroxide in 10 ml of water are added slowly in succession to 7.6 mmol (1.25 g) of phenylalanine and 7.6 mmol (0.3 g) of sodium hydroxide in 10 ml of water. The reaction mixture is stirred for 1 hour at room temperature. After decanting, the aqueous phase is washed with dichloromethane and rendered acidic to pH=2 with a dilute hydrochloric acid solution. After extraction with dichloromethane, the organic phase is dried over sodium sulphate and concentrated to yield the expected product.

Step b: N2-[1-Benzyl-2-oxo-2-(2-phenylhydrazino)ethyl]-2-naphthalenesulphonamide The expected product is obtained according to the process described in Example 1, Step b, using the compound described in the preceding Step as starting material.

| Elemental microanalysis: | C | H | N |
|---|---|---|---|
| % calculated | 67.41 | 5.17 | 9.44 |
| % found | 67.03 | 5.34 | 9.57 |

EXAMPLE 11

N2-[2-(2-Benzoylhydrazino)-1-benzyl-2-oxoethyl]-2-naphthalene-sulphonamide

The expected product is obtained according to the process described in Example 1, Step b, using the compound described in Example 10, Step a, as starting material, and replacing phenylhydrazine by phenylhydrazide.

Melting point: 239–240° C.
| Elemental microanalysis: | C | H | N |
|---|---|---|---|
| % calculated | 65.96 | 4.86 | 8.87 |
| % found | 65.55 | 4.99 | 8.88 |

EXAMPLE 12

N2-[1-Benzyl-2-oxo-2-(2-phenylhydrazino)ethyl]-2-naphthylamide

The expected product is obtained according to the process described in Example 1, in Step a replacing benzyl chloroformate by naphthoyl chloride.

| Elemental microanalysis: | C | H | N |
|---|---|---|---|
| % calculated | 76.28 | 5.62 | 10.27 |
| % found | 76.25 | 5.76 | 10.03 |

EXAMPLE 13

N2-[2-(2-Benzoylhydrazino)-1-benzyl-2-oxoethyl]-2-naphthylamide

The expected product is obtained according to the process described in Example 1, in Step a replacing benzyl chloroformate by naphthoyl chloride, and in Step b replacing phenylhydrazine by phenylhydrazide.

| Elemental microanalysis: | C | H | N |
|---|---|---|---|
| % calculated | 74.17 | 5.26 | 9.61 |
| % found | 74.21 | 5.38 | 9.49 |

EXAMPLE 14

N2-[1-Benzyl-2-oxo-2-(2-nicotinoylhydrazino)ethyl]-2-naphthylamide

The expected product is obtained according to the process described in Example 1, in Step a replacing benzyl chloroformate by naphthoyl chloride, and in Step b replacing phenylhydrazine by 3-pyridinecarbohydrazide.

| Elemental microanalysis: | C | H | N |
|---|---|---|---|
| % calculated | 71.23 | 5.02 | 12.79 |
| % found | 70.97 | 5.38 | 12.61 |

EXAMPLE 15

N2-{1-Benzyl-2-[2-(2-indolecarbonyl)hydrazino]-2-oxoethyl}-2-naphthylamide

The expected product is obtained according to the process described in Example 1, in Step a replacing benzyl chloroformate by naphthoyl chloride, and in Step b replacing phenylhydrazine by 2-indolecarbohydrazide.

Melting point: 214–215° C.
| Elemental microanalysis: | C | H | N |
|---|---|---|---|
| % calculated | 73.11 | 5.25 | 11.76 |
| % found | 72.98 | 5.16 | 11.75 |

EXAMPLE 16

N1-[1-Benzyl-2-oxo-2-(2-phenylhydrazino)ethyl]-1-benzenesulphonamide

Step a: 2-(Phenylsulphonylamino)-3-phenylpropanoic acid

A mixture of 151 mmol (26.6 g) of benzenesulphonyl chloride and 50 ml of 4M aqueous sodium hydroxide is added to a solution of 37.8 mmol (6.25 g) of phenylalanine in 50 ml of 4M aqueous sodium hydroxide. The reaction mixture is stirred at room temperature for 24 hours. The solution is then rendered acidic to pH=2 with dilute hydrochloric acid and extracted with ether. The organic phase is dried over magnesium sulphate and concentrated. The resulting residue is recrystallised from ethanol to yield the expected compound.

Step b: N1-[1-Benzyl-2-oxo-2-(2-phenylhydrazino)ethyl]-1-benzenesulphonamide

The expected product is obtained according to the process described in Example 1, Step b, using the compound described in the preceding Step as starting material.

Melting point: 162–163° C.
Elemental microanalysis:

|  | C | H | N |
|---|---|---|---|
| % calculated | 63.80 | 5.32 | 10.63 |
| % found | 63.03 | 5.38 | 10.38 |

EXAMPLE 17

N1-[2-(2-Benzoylhydrazino)-1-benzyl-2-oxoethyl]-1-benzenesulphonamide

The expected product is obtained according to the process described in Example 1, Step b, using the compound of Example 16, Step a, as starting material, and replacing phenylhydrazine by phenylhydrazide.

Melting point: 200° C.
Elemental microanalysis:

|  | C | H | N |
|---|---|---|---|
| % calculated | 62.41 | 4.96 | 9.93 |
| % found | 62.59 | 5.06 | 9.84 |

EXAMPLE 18

N1-[1-Benzyl-2-oxo-2-(2-phenylhydrazino)ethyl]-1-(4-chlorobenzene)sulphonamide

The expected product is obtained according to the process described in Example 10, in Step a replacing 2-naphthylsulphonyl chloride by 4-chlorobenzenesulphonyl chloride.

Melting point: 174–175° C.
Elemental microanalysis:

|  | C | H | N |
|---|---|---|---|
| % calculated | 58.67 | 4.66 | 9.78 |
| % found | 58.63 | 4.77 | 9.70 |

EXAMPLE 19

N1-[2-(2-Benzoylhydrazino)-1-benzyl-2-oxoethyl]-1-(4-chlorobenzene)sulphonamide

The expected product is obtained according to the process described in Example 10, in Step a replacing 2-naphthylsulphonyl chloride by 4-chlorobenzenesulphonyl chloride, and in Step b replacing phenylhydrazine by phenylhydrazide.

Melting point: 192–193° C.
Elemental microanalysis:

|  | C | H | N |
|---|---|---|---|
| % calculated | 57.70 | 4.37 | 9.18 |
| % found | 57.50 | 4.43 | 9.14 |

EXAMPLE 20

N1-[1-Benzyl-2-oxo-2-(2-phenylhydrazino)ethyl]-1-(3,4-dichlorobenzene)sulphonamide The expected product is obtained according to the process described in Example 16, in Step a replacing benzenesulphonyl chloride by 3,4-dichlorobenzenesulphonyl chloride.

Melting point: 164–165° C.
Elemental microanalysis:

|  | C | H | N |
|---|---|---|---|
| % calculated | 54.32 | 4.12 | 9.05 |
| % found | 54.14 | 4.16 | 8.87 |

EXAMPLE 21

N1-[2-(2-Benzoylhydrazino)-1-benzyl-2-oxoethyl]-1-(3,4-dichlorobenzene)sulphonamide The expected product is obtained according to the process described in Example 16, in Step a replacing benzenesulphonyl chloride by 3,4-dichlorobenzenesulphonyl chloride, and in Step b replacing phenylhydrazine by phenylhydrazide.

Melting point: 200–201° C.
Elemental microanalysis:

|  | C | H | N |
|---|---|---|---|
| % calculated | 53.66 | 3.86 | 8.54 |
| % found | 53.45 | 3.93 | 8.28 |

EXAMPLE 22

Benzyl N-[1-(4-methoxybenzyl)-2-oxo-2-(2-phenylhydrazino)ethyl]-carbamate

The expected product is obtained according to the process described in Example 1, in Step a replacing phenylalanine by O-methyltyrosine.

Melting point: 182–185° C.
Elemental microanalysis:

|  | C | H | N |
|---|---|---|---|
| % calculated | 68.74 | 5.97 | 10.02 |
| % found | 68.56 | 6.11 | 9.81 |

EXAMPLE 23

Benzyl N-[2-benzoylhydrazino-1-methoxybenzyl)-2-oxoethyl]carbamate

The expected product is obtained according to the process described in Example 1, in Step a replacing phenylalanine by O-methyltyrosine, and in Step b replacing phenylhydrazine by phenylhydrazide.

Melting point: 208–209° C.
Elemental microanalysis:

|  | C | H | N |
|---|---|---|---|
| % calculated | 67.11 | 5.59 | 9.40 |
| % found | 67.19 | 5.74 | 9.32 |

EXAMPLE 24

Benzyl N-{2-[2-(2-indolylcarbonyl)hydrazino]-1-(4-methoxybenzyl)-2-oxoethyl}carbamate The expected product is obtained according to the process described in Example 1, in Step a replacing phenylalanine by O-methyltyrosine, and in Step b replacing phenylhydrazine by 2-indolecarbohydrazide.

Melting point: 185–186° C.
Elemental microanalysis:

|  | C | H | N |
|---|---|---|---|
| % calculated | 66.67 | 5.35 | 11.52 |
| % found | 66.40 | 5.43 | 12.87 |

EXAMPLE 25

Benzyl N-[1-(4-methoxybenzyl)-2-(2-nicotinoylhydrazino)-2-oxoethyl]carbamate

The expected product is obtained according to the process described in Example 1, in Step a replacing phenylalanine by O-methyltyrosine, and in Step b replacing phenylhydrazine by 3-pyridinecarbohydrazide.

Elemental microanalysis:

|  | C | H | N |
|---|---|---|---|
| % calculated | 64.29 | 5.36 | 12.50 |
| % found | 64.43 | 5.52 | 12.14 |

EXAMPLE 26

Benzyl N-(2-{2-[2-(3-indolyl)acetyl]hydrazino}-1-(4-methoxybenzyl)-2-oxoethyl)carbamate The expected product is obtained according to the process described in Example 1, in Step a replacing phenylalanine by O-methyltyrosine, and in Step b replacing phenylhydrazine by 3-indolylacetohydrazide.

Melting point: 194–195° C.
Elemental microanalysis:

|  | C | H | N |
|---|---|---|---|
| % calculated | 67.20 | 5.60 | 11.19 |
| % found | 67.01 | 5.59 | 11.12 |

EXAMPLE 27

N1-[1-(4-Methoxybenzyl)-2-oxo-2-(2-phenylhydrazino)ethyl]-2-phenoxyacetamide

The expected product is obtained according to the process described in Example 5, in Step a replacing phenylalanine by O-methyltyrosine.

Elemental microanalysis:

|  | C | H | N |
|---|---|---|---|
| % calculated | 68.74 | 5.97 | 10.02 |
| % found | 68.37 | 6.06 | 9.86 |

EXAMPLE 28

N1-[2-(2-Benzoylhydrazino)-1-(4-methoxybenzyl)-2-oxoethyl]-2-phenoxyacetamide

The expected product is obtained according to the process described in Example 5, in Step a replacing phenylalanine by O-methyltyrosine, and in Step b replacing phenylhydrazine by phenylhydrazide.

Elemental microanalysis:

|  | C | H | N |
|---|---|---|---|
| % calculated | 67.11 | 5.59 | 9.40 |
| % found | 67.19 | 5.81 | 9.60 |

EXAMPLE 29

N1-[1-(4-Methoxybenzyl)-2-(2-nicotinoylhydrazino)-2-oxoethyl]-2-phenoxyacetamide The expected product is obtained according to the process described in Example 5, in Step a replacing phenylalanine by O-methyltyrosine, and in Step b replacing phenylhydrazine by 3-pyridinecarbohydrazide.

Elemental microanalysis:

|  | C | H | N |
|---|---|---|---|
| % calculated | 64.29 | 5.36 | 12.50 |
| % found | 64.06 | 5.34 | 12.34 |

EXAMPLE 30

N2-[1-(4-Methoxybenzyl)-2-oxo-2-(2-phenylhydrazino)ethyl]-2-naphthalenesulphonamide The expected product is obtained according to the process described in Example 10, replacing phenylalanine by O-methyltyrosine.

Melting point: 210–212° C.
Elemental microanalysis:

|  | C | H | N |
|---|---|---|---|
| % calculated | 64.47 | 5.37 | 8.87 |
| % found | 64.17 | 5.25 | 8.56 |

EXAMPLE 31

N2-[2-(2-Benzoylhydrazino)-1-(4-methoxybenzyl)-2-oxoethyl]-2-naphthalenesulphonamide The expected product is obtained according to the process described in Example 10, in Step a replacing phenylalanine by O-methyltyrosine, and in Step b replacing phenylhydrazine by phenylhydrazide.

Melting point: 246–247° C.
Elemental microanalysis:

|  | C | H | N |
|---|---|---|---|
| % calculated | 63.28 | 5.07 | 8.20 |
| % found | 63.14 | 5.01 | 8.55 |

EXAMPLE 32

N2-[1-(4-Methoxybenzyl)-2-oxo-2-(2-phenylhydrazino)ethyl]-2-naphthylamide

The expected product is obtained according to the process described in Example 1, in Step a replacing phenylalanine by O-methyltyrosine and benzyl chloroformate by naphthoyl chloride.

Elemental microanalysis:

|  | C | H | N |
|---|---|---|---|
| % calculated | 73.80 | 5.70 | 9.57 |
| % found | 73.53 | 5.62 | 9.54 |

EXAMPLE 33

N2-[1-(4-Methoxybenzyl)-2-(2-nicotinoylhydrazino)-2-oxoethyl]-2-naphthylamide

The expected product is obtained according to the process described in Example 1, in Step a replacing phenylalanine by O-methyltyrosine and benzyl chloroformate by naphthoyl chloride, and in Step b replacing phenylhydrazide by 3-pyridinecarbohydrazide.

Elemental microanalysis:

|  | C | H | N |
|---|---|---|---|
| % calculated | 69.23 | 5.13 | 11.97 |
| % found | 69.25 | 5.13 | 11.72 |

EXAMPLE 34

N1-[1-(4-Methoxybenzyl)-2-oxo-2-(2-phenylhydrazino)ethyl]-1-benzenesulphonamide

The expected product is obtained according to the process described in Example 16, in Step a replacing L-phenylalanine by O-methyltyrosine.

Melting point: 163–164° C.
Elemental microanalysis:

|  | C | H | N |
|---|---|---|---|
| % calculated | 62.12 | 5.41 | 9.88 |
| % found | 61.71 | 5.54 | 9.89 |

EXAMPLE 35

N1-[2-(2-Benzoylhydrazino)-1-(4-methoxybenzyl)-2-oxoethyl]-1-benzenesulphonamide The expected product is obtained according to the process described in Example 16, in Step a replacing L-phenylalanine by O-methyltyrosine, and in Step b replacing phenylhydrazine by phenylhydrazide.

Elemental microanalysis:

|  | C | H | N |
|---|---|---|---|
| % calculated | 60.85 | 5.07 | 6.26 |
| % found | 60.81 | 5.23 | 9.20 |

EXAMPLE 36

N1-[1-(4-Methoxybenzyl)-2-oxo-2-(2-phenylhydrazino)ethyl]-1-(4-chlorobenzene)sulphonamide The expected product is obtained according to the process described in Example 10, in Step a replacing phenylalanine by O-methyltyrosine and 2-naphthylsulphonyl chloride by 4-chlorobenzenesulphonyl chloride.

Melting point: 181–183° C.
Elemental microanalysis:

|  | C | H | N |
|---|---|---|---|
| % calculated | 56.31 | 4.92 | 9.39 |
| % found | 56.64 | 4.85 | 9.02 |

EXAMPLE 37

N1-[2-(2-Benzoylhydrazino)-1-(4-methoxybenzyl)-2-oxoethyl]-1-(4-chlorobenzene)sulphonamide The expected product is obtained according to the process described in Example 10, in Step a replacing phenylalanine by O-methyltyrosine and 2-naphthylsulphonyl chloride by 4-chlorobenzenesulphonyl chloride, and in Step b replacing phenylhydrazine by phenylhydrazide.

Elemental microanalysis:

|  | C | H | N |
|---|---|---|---|
| % calculated | 56.61 | 4.54 | 8.61 |
| % found | 56.82 | 4.55 | 8.61 |

EXAMPLE 38

N1-[1-(4-Methoxybenzyl)-2-oxo-2-(2-phenylhydrazino)ethyl]-1-(3,4-dichlorobenzene)sulphonamide The expected product is obtained according to the process described in Example 16, in Step a replacing phenylalanine by O-methyltyrosine and benzenesulphonyl chloride by 3,4-dichlorobenzenesulphonyl chloride.

Melting point: 153–154° C.
Elemental microanalysis:

|  | C | H | N |
|---|---|---|---|
| % calculated | 53.44 | 4.25 | 8.50 |
| % found | 53.80 | 4.38 | 8.30 |

EXAMPLE 39

N1-[2-(2-Benzoylhydrazino)-1-(4-methoxybenzyl)-2-oxoethyl]-1-(3,4-dichlorobenzene)sulphonamide The expected product is obtained according to the process described in Example 16, in Step a replacing phenylalanine by O-methyltyrosine and benzenesulphonyl chloride by 3,4-dichlorobenzenesulphonyl chloride, and in Step b replacing phenylhydrazine by phenyl-hydrazide.

Melting point: 214–215° C.
Elemental microanalysis:

|  | C | H | N |
|---|---|---|---|
| % calculated | 52.87 | 4.03 | 8.05 |
| % found | 52.60 | 4.09 | 8.17 |

EXAMPLE 40

N2-[6-Oxo-6-(2-phenylhydrazino)hexyl]-2-naphthalenesulphonamide

Step a: 6-[(2-Naphthylsulphonyl)amino]hexanoic acid 30.5 mmol (6.42 g) of 2-naphthylsulphonyl chloride and 15 ml of 4M aqueous sodium hydroxide are added in succession to a solution of 15.2 mmol (2 g) of 6-aminocaproic acid in 15 ml of 4M aqueous sodium hydroxide. The reaction mixture is stirred at room temperature for 24 hours. The solution is then rendered acidic to pH=2 with concentrated hydrochloric acid, and extracted with dichloromethane. The organic phase is dried over sodium sulphate and concentrated, and the resulting residue is recrystallised from hexane to yield the expected compound.

Step b: N2-[6-Oxo-6-(2-phenylhydrazino)hexyl]-2-naphthalenesulphonamide

The expected product is obtained according to the process described in Example 1, Step b, using the compound described in the preceding Step as starting material.

Elemental microanalysis:

|  | C | H | N |
|---|---|---|---|
| % calculated | 64.16 | 6.08 | 10.21 |
| % found | 64.23 | 5.88 | 9.95 |

EXAMPLE 41

N2-[6-(2-Benzoylhydrazino)-6-oxohexyl]-2-naphthalene-sulphonamide

The expected product is obtained according to the process described in Example 40, in Step b replacing phenylhydrazine by phenylhydrazide.

Elemental microanalysis:

|  | C | H | N |
|---|---|---|---|
| % calculated | 62.79 | 5.69 | 9.56 |
| % found | 62.50 | 5.70 | 9.49 |

EXAMPLE 42

N2-[6-(2-Benzoylhydrazino)-6-oxohexyl]-2-(2-nitrophenyl)sulphonamide

The expected product is obtained according to the process described in Example 40, in Step a replacing 2-naphthylsulphonyl chloride by 2-nitrophenylsulphonyl chloride.

Melting point: 106° C.
Elemental microanalysis:

|  | C | H | N |
|---|---|---|---|
| % calculated | 52.53 | 5.10 | 12.89 |
| % found | 52.61 | 5.14 | 12.76 |

EXAMPLE 43

N2-({4-[(2-Phenylhydrazino)carbonyl]cyclohexyl}methyl)-2-naphthalenesulphonamide The expected product is obtained according to the process described in Example 40, in Step a replacing 6-aminocaproic acid by 4-(aminomethyl)cyclohexanecarboxylic acid.

| | C | H | N |
|---|---|---|---|
| Elemental microanalysis: (x½ H₂O) | | | |
| % calculated | 64.50 | 6.27 | 9.41 |
| % found | 64.54 | 6.04 | 9.22 |

EXAMPLE 44

N2-({4-[(2-Benzoylhydrazino)carbonyl]cyclohexyl}methyl)-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by phenylhydrazide.

| | C | H | N |
|---|---|---|---|
| Elemental microanalysis: (x½ H₂O) | | | |
| % calculated | 63.22 | 5.90 | 8.85 |
| % found | 63.59 | 5.68 | 8.76 |

EXAMPLE 45

N2-[(4-{[2-(2-Indolylcarbonyl)hydrazino]carbonyl}cyclohexyl)-methyl]-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by 2-indolylcarbohydrazide.

| | C | H | N |
|---|---|---|---|
| Elemental microanalysis: (x½ H₂O) | | | |
| % calculated | 63.11 | 5.45 | 10.90 |
| % found | 63.11 | 5.72 | 11.10 |

EXAMPLE 46

N2-({4-[(2-Nicotinoylhydrazino)carbonyl]cyclohexyl}methyl)-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by 3-pyridinecarbohydrazide.

Melting point: 204–205° C.

| | C | H | N |
|---|---|---|---|
| Elemental microanalysis: | | | |
| % calculated | 61.76 | 5.57 | 12.01 |
| % found | 62.15 | 5.68 | 11.88 |

EXAMPLE 47

N2-{[4-({2-[2-(3-Indolyl)-acetyl]hydrazino}carbonyl)cyclohexyl]-methyl}-2-naphthalenesulphonamide The expected product is obtained according to the process described in Example 40, in Step a replacing 6-aminocaproic acid by 4-(aminomethyl)cyclohexanecarboxylic acid, and in Step b replacing phenylhydrazine by 3-indolylacetohydrazide.

| | C | H | N |
|---|---|---|---|
| Elemental microanalysis: | | | |
| % calculated | 62.61 | 5.77 | 10.44 |
| % found | 62.11 | 5.99 | 10.41 |

EXAMPLE 48

N1-({4-[(2-Phenylhydrazino)carbonyl]cyclohexyl}methyl)-1-benzylsulphonamide

The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride.

Melting point: 194–196° C.

| | C | H | N |
|---|---|---|---|
| Elemental microanalysis: | | | |
| % calculated | 61.99 | 6.50 | 10.84 |
| % found | 62.81 | 6.60 | 10.83 |

EXAMPLE 49

N1-({4-[(2-Benzoylhydrazino)carbonyl]cyclohexyl}methyl)-1-benzenesulphonamide

The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by phenylhydrazide.

| | C | H | N |
|---|---|---|---|
| Elemental microanalysis: | | | |
| % calculated | 60.70 | 6.06 | 10.11 |
| % found | 60.25 | 6.24 | 10.07 |

EXAMPLE 50

N1-({4-[(2-Nicotinoylhydrazino)carbonyl]cyclohexyl}methyl)-1-benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by 3-pyridinecarbohydrazide.

Melting point: 213–215° C.
Elemental microanalysis: (x½ H₂O)

|  | C | H | N |
|---|---|---|---|
| % calculated | 56.41 | 5.64 | 13.16 |
| % found | 56.45 | 5.74 | 13.56 |

EXAMPLE 51

N1-[(4-{[2-(4-Chlorophenyl)hydrazino]carbonyl}cyclohexyl)methyl]-1-benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by 4-chlorophenylhydrazine.

Elemental microanalysis:

|  | C | H | N |
|---|---|---|---|
| % calculated | 56.93 | 5.73 | 9.96 |
| % found | 56.91 | 5.82 | 9.86 |

EXAMPLE 52

N1-[(4-{2-(4-Chlorobenzoyl)hydrazino]carbonyl}cyclohexyl)methyl]-1-benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by benzenesulphonyl chloride, and in Step b replacing phenyl-hydrazine by 4-chlorophenylhydrazine.

Elemental microanalysis:

|  | C | H | N |
|---|---|---|---|
| % calculated | 56.01 | 5.33 | 9.33 |
| % found | 55.98 | 5.43 | 9.41 |

EXAMPLE 53

N1-({4-[(2-Phenylhydrazino)carbonyl]cyclohexyl}methyl)-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride.

Elemental microanalysis:

|  | C | H | N |
|---|---|---|---|
| % calculated | 55.54 | 5.59 | 12.95 |
| % found | 55.35 | 5.49 | 12.70 |

EXAMPLE 54

N1-({4-[(2-Benzoylhydrazino)carbonyl]cyclohexyl}methyl)-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride, and in Step b replacing phenylhydrazine by phenylhydrazide.

Elemental microanalysis: (x½ H₂O)

|  | C | H | N |
|---|---|---|---|
| % calculated | 53.72 | 5.15 | 11.93 |
| % found | 53.57 | 5.19 | 11.76 |

EXAMPLE 55

N1-{[4-(2-[2-(3-Indolyl)-acetyl]hydrazino}carbonyl)cyclohexyl]-methyl}-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride, and in Step b replacing phenylhydrazine by 3-indolylacetohydrazide.

Elemental microanalysis: (x½ H₂O)

|  | C | H | N |
|---|---|---|---|
| % calculated | 55.11 | 5.17 | 13.39 |
| % found | 55.13 | 5.14 | 13.35 |

EXAMPLE 56

N1-[(4-[2-(2-Indolylcarbonyl)hydrazino]carbonyl}cyclohexyl)-methyl]-1-(2-nitrobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitrobenzenesulphonyl chloride, and in Step b replacing phenylhydrazine by 2-indolylcarbohydrazide.

Melting point: 249–251° C.
Elemental microanalysis:

|  | C | H | N |
|---|---|---|---|
| % calculated | 55.27 | 5.01 | 14.02 |
| % found | 55.02 | 5.28 | 14.39 |

EXAMPLE 57

N1-({4-[(2-Benzoylhydrazino)carbonyl]cyclohexyl}methyl)-1-(2-nitro-4-trifluoromethylphenyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-nitro-4-trifluoromethylphenylsulphonyl chloride, and in Step b replacing phenylhydrazine by phenylhydrazide.

Elemental microanalysis:

|  | C | H | N |
|---|---|---|---|
| % calculated | 50.00 | 4.36 | 10.61 |
| % found | 49.97 | 4.46 | 10.68 |

EXAMPLE 58

N1-({4-[(2-Phenylhydrazino)carbonyl]cyclohexyl}methyl)-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride.

Melting point: 192–194° C.
Elemental microanalysis: (x½ H₂O)

|  | C | H | N |
|---|---|---|---|
| % calculated | 50.48 | 5.05 | 8.83 |
| % found | 50.38 | 5.15 | 8.69 |

EXAMPLE 59

N1-({4-[(2-Benzoylhydrazino)carbonyl]cyclohexyl}methyl)-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride, and in Step b replacing phenylhydrazine by phenylhydrazide.

Melting point: 251–253° C.
Elemental microanalysis.:

|  | C | H | N |
|---|---|---|---|
| % calculated | 51.02 | 4.89 | 8.50 |
| % found | 50.47 | 4.92 | 8.34 |

EXAMPLE 60

N1-[(4-{[2-(4-Chlorophenyl)hydrazino]cyclohexyl}carbonyl)methyl]-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride, and in Step b replacing phenylhydrazine by 4-chlorophenylhydrazine.

Elemental microanalysis:

|  | C | H | N |
|---|---|---|---|
| % calculated | 47.96 | 4.63 | 8.39 |
| % found | 47.99 | 4.63 | 8.29 |

EXAMPLE 61

N1-[(4-{[2-(4-Chlorobenzoyl)hydrazino]cyclohexyl}carbonyl)methyl]-1-(4-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride, and in Step b replacing phenylhydrazine by 4-chlorophenylhydrazide.

Elemental microanalysis:

|  | C | H | N |
|---|---|---|---|
| % calculated | 47.69 | 4.38 | 7.95 |
| % found | 47.78 | 4.45 | 8.05 |

EXAMPLE 62

N'-Phenyl-1-(phenylsulphonyl)perhydro-2-indolecarbohydrazide

Step a: 1-(Phenylsulphonyl)-2-perhydroindolecarboxylic acid 29.8 mmol (3.8 ml) of benzenesulphonyl chloride and 7.4 ml of 4M sodium hydroxide solution are added in succession to a solution, cooled to 0° C., of 29.6 mmol (5 g) of 2-perhydroindolecarboxylic acid in 7.4 ml of 4M NaOH. The reaction mixture is left at room temperature, with stirring, for 24 hours. The mixture is then rendered acidic to pH 2–3 and filtered. The resulting solid is washed with ether to yield the expected product.

Step b: N'-Phenyl-1-(phenylsulphonyl)perhydro-2-indolecarbohydrazide

The expected product is obtained according to the process described in Step b of Example 1, using the compound described in the preceding Step as starting material.

Elemental microanalysis:

|  | C | H | N |
|---|---|---|---|
| % calculated | 63.16 | 6.27 | 10.53 |
| % found | 63.37 | 6.43 | 10.38 |

EXAMPLE 63

N'-(2-Indolylcarbonyl)-1-(phenylsulphonyl) perhydro-2-indolecarbohydrazide

The expected product is obtained according to the process described in Example 62, in Step b replacing phenylhydrazine by 2-indolecarbohydrazide.

Melting point: 134–137° C.
Elemental microanalysis:

|  | C | H | N |
|---|---|---|---|
| % calculated | 61.80 | 5.58 | 12.02 |
| % found | 61.34 | 5.74 | 11.62 |

EXAMPLE 64

N'-Nicotinoyl-1-(phenylsulphonyl)perhydro-2-indolecarbohydrazide

The expected product is obtained according to the process described in Example 62, in Step b replacing phenylhydrazine by 3-pyridinecarbohydrazide.

Elemental microanalysis:

|  | C | H | N |
|---|---|---|---|
| % calculated | 58.88 | 5.61 | 13.08 |
| % found | 58.41 | 5.74 | 13.64 |

EXAMPLE 65

N2-({4-[(2-Phenylhydrazino)carbonyl] cyclohexyl}methyl)-1-naphthalenesulphonamide Step a: 6-(1-Naphthylsulphonyl)aminomethyl] cyclohexanecarboxylic acid The expected product is obtained according to the process described in Example 40, Step a, replacing 6-aminocaproic acid by 4-(aminomethyl)cyclohexanecarboxylic acid and using 1-naphthylsulphonyl chloride.

Step b: N2-({4-[(2-Phenylhydrazino)carbonyl] cyclohexyl}methyl)-1-naphthalenesulphonamide The expected product is obtained according to the process described in Example 1, Step b, using the compound described in the preceding Step as starting material, and replacing phenylhydrazine by phenylhydrazide.

Elemental microanalysis:

|  | C | H | N |
|---|---|---|---|
| % calculated | 64.44 | 5.80 | 9.02 |
| % found | 64.59 | 5.96 | 8.76 |

EXAMPLE 66

N1-({4-[(2-Benzoylhydrazino)carbonyl] cyclohexyl}methyl)-1-(4-isopropylbenzene) sulphonamide The expected product is obtained according to the process described in Example 40, in Step a replacing 6-aminocaproic acid by 4-(aminomethyl) cyclohexanecarboxylic acid and 2-naphthylsulphonyl chloride by 4-isopropylbenzenesulphonyl chloride, and in Step b replacing phenylhydrazine by phenylhydrazide.

Melting point: 232–236° C.
Elemental microanalysis:

|  | C | H | N |
|---|---|---|---|
| % calculated | 62.46 | 6.77 | 9.10 |
| % found | 62.32 | 7.20 | 9.18 |

EXAMPLE 67

N1-({4-[(2-Naphthoylhydrazino)carbonyl] cyclohexyl}methyl)-1-(2-nitrobenzene) sulphonamide The expected product is obtained according to the process described in Example 40, in Step a replacing 6-aminocaproic acid by 4-(aminomethyl) cyclohexanecarboxylic acid and 2-naphthylsulphonyl chloride by 2-nitrobenzenesulphonyl choride, and in Step b replacing phenylhydrazine by 2-naphthylhydrazide.

Melting point: 263–264° C.
Elemental microanalysis:

|  | C | H | N |
|---|---|---|---|
| % calculated | 58.81 | 5.13 | 10.97 |
| % found | 58.87 | 5.32 | 11.25 |

EXAMPLE 68

N1-({4-[(2-Benzoylhydrazino)carbonyl] cyclohexyl}methyl)-1-(3-nitrobenzene) sulphonamide The expected product is obtained according to the process described in Example 54, replacing 2-nitrobenzenesulphonyl chloride by 3-nitrobenzenesulphonyl chloride.

Melting point: 198–201° C.
Elemental microanalysis:

|  | C | H | N |
|---|---|---|---|

| | | | |
|---|---|---|---|
| % calculated | 51.69 | 4.92 | 11.48 |
| % found | 51.58 | 4.83 | 11.61 |

EXAMPLE 69

N1-({4-[(2-Phenylhydrazino)carbonyl]cyclohexyl}methyl)-1-(4-nitrobenzene) sulphonamide The expected product is obtained according to the process described in Example 53, replacing 2-nitrobenzenesulphonyl chloride by 4-nitrobenzenesulphonyl chloride.

Melting point: 200–201° C.
Elemental microanalysis:

| | C | H | N |
|---|---|---|---|
| % calculated | 54.36 | 5.44 | 12.68 |
| % found | 53.99 | 5.33 | 12.46 |

EXAMPLE 70

N1-({4-[(2-Benzoylhydrazino)carbonyl]cyclohexyl}methyl)-1-(4-nitrobenzene) sulphonamide The expected product is obtained according to the process described in Example 54, replacing 2-nitrobenzenesulphonyl chloride by 4-nitrobenzenesulphonyl chloride.

Melting point: 262–264° C.
Elemental microanalysis:

| | C | H | N |
|---|---|---|---|
| % calculated | 53.67 | 5.11 | 11.93 |
| % found | 53.68 | 5.21 | 11.96 |

EXAMPLE 71

N1-[(4-{[2-(4-Chlorophenyl)hydrazino]carbonyl}cyclohexyl)-methyl]-1-(4-nitrobenzene) sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-nitrobenzenesulphonyl chloride, and in Step b replacing phenylhydrazine by 4-chlorophenylhydrazine.

Melting point: 211–213° C.
Elemental microanalysis:

| | C | H | N |
|---|---|---|---|
| % calculated | 51.45 | 4.96 | 12.00 |
| % found | 51.52 | 5.12 | 11.81 |

EXAMPLE 72

N1-[(4-{[2-(4-Chlorobenzoyl)hydrazino]carbonyl}cyclohexyl)-methyl]-1-(4-nitrobenzene) sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-nitrobenzenesulphonyl chloride, and in Step b replacing phenylhydrazine by 4-chlorophenylhydrazide.

Melting point: 272–273° C.
Elemental microanalysis:

| | C | H | N |
|---|---|---|---|
| % calculated | 50.91 | 4.65 | 11.31 |
| % found | 50.89 | 4.76 | 11.29 |

EXAMPLE 73

N1-({4-[(2-(4-Phenylhydrazino)carbonyl]cyclohexyl}methyl)-1-(2-bromobenzene) sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride.

Melting point: 165–167° C.
Elemental microanalysis:

| | C | H | N |
|---|---|---|---|
| % calculated | 51.46 | 5.14 | 9.01 |
| % found | 51.54 | 5.29 | 9.03 |

EXAMPLE 74

N1-({4-[(2-Benzoylhydrazino)carbonyl]cyclohexyl}methyl)-1-(2-bromobenzene) sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride, and in Step b replacing phenylhydrazine by phenylhydrazide.

| | C | H | N |
|---|---|---|---|
| Melting point: 231–232° C. | | | |
| Elemental microanalysis: | | | |
| % calculated | 50.97 | 4.85 | 8.49 |
| % found | 51.11 | 4.98 | 8.51 |

EXAMPLE 75

N1-[(4-{[(2-(4-Chlorophenyl)hydrazino]carbonyl}cyclohexyl)-methyl]-1-(2-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride, and in Step b replacing phenylhydrazine by 4-chlorophenylhydrazine.

| Elemental microanalysis: | | | |
|---|---|---|---|
| | C | H | N |
| % calculated | 47.92 | 4.59 | 8.39 |
| % found | 48.15 | 4.73 | 8.37 |

EXAMPLE 76

N1-[(4-{[2-(4-Chlorophenyl)hydrazino]cyclohexyl}carbonyl)-methyl]-1-(2-bromobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-bromobenzenesulphonyl chloride, and in Step b replacing phenylhydrazine by 4-chlorophenylhydrazide.

| | C | H | N |
|---|---|---|---|
| Melting point: 263–264° C. | | | |
| Elemental microanalysis: | | | |
| % calculated | 47.65 | 4.35 | 7.94 |
| % found | 47.65 | 4.44 | 7.87 |

EXAMPLE 77

N1-({4-[(2-Benzoylhydrazino)carbonyl]cyclohexyl}methyl)-1-(4-chlorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-chlorobenzenesulphonyl chloride, and in Step b replacing phenylhydrazine by phenylhydrazide.

| | C | H | N |
|---|---|---|---|
| Melting point: 254–256° C. | | | |
| Elemental microanalysis: | | | |
| % calculated | 56.01 | 5.33 | 9.33 |
| % found | 56.00 | 5.22 | 9.24 |

EXAMPLE 78

N1-({4-[(2-Benzoylhydrazino)carbonyl]cyclohexyl}methyl)-1-(3,4-dichlorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 3,4-dichlorobenzenesulphonyl chloride, and in Step b replacing phenylhydrazine by phenylhydrazide.

| | C | H | N |
|---|---|---|---|
| Melting point: 251–252° C. | | | |
| Elemental microanalysis: | | | |
| % calculated | 52.07 | 4.75 | 8.67 |
| % found | 51.91 | 5.32 | 8.71 |

EXAMPLE 79

N1-({4-[(2-Phenylhydrazino)carbonyl]cyclohexyl}methyl)-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride.

| | C | H | N |
|---|---|---|---|
| Melting point: 192–193° C. | | | |
| Elemental microanalysis: | | | |
| % calculated | 59.19 | 5.92 | 10.36 |
| % found | 59.03 | 5.98 | 10.23 |

EXAMPLE 80

N1-({4-([(2-Benzoylhydrazino)carbonyl]cyclohexyl}methyl)-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride, and in Step b replacing phenylhydrazine by phenylhydrazide.

Melting point: 264–265° C.
Elemental microanalysis:

|  | C | H | N |
|---|---|---|---|
| % calculated | 58.13 | 5.54 | 9.69 |
| % found | 58.04 | 5.60 | 9.71 |

EXAMPLE 81

N1-[(4-{[2-(4-Chlorophenyl)hydrazino]carbonyl}cyclohexyl)-methyl]-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride, and in Step b replacing phenylhydrazine by 4-chlorophenylhydrazine.

Melting point: 216–217° C.
Elemental microanalysis:

|  | C | H | N |
|---|---|---|---|
| % calculated | 54.31 | 5.20 | 9.50 |
| % found | 54.39 | 5.22 | 9.45 |

EXAMPLE 82

N1-[(4-{[2-(4-Chlorobenzoyl)hydrazino]carbonyl}cyclohexyl)-methyl]-1-(4-fluorobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-fluorobenzenesulphonyl chloride, and in Step b replacing phenylhydrazine by 4-chlorophenylhydrazide.

Melting point: 257–258° C.
Elemental microanalysis:

|  | C | H | N |
|---|---|---|---|
| % calculated | 53.85 | 4.92 | 8.98 |
| % found | 53.90 | 5.00 | 8.89 |

EXAMPLE 83

N1-({4-[(2-Benzoylhydrazino)carbonyl]cyclohexyl}methyl)-1-(4-methylbenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-methylbenzenesulphonyl chloride, and in Step b replacing phenylhydrazine by phenylhydrazide.

Elemental microanalysis:

|  | C | H | N |
|---|---|---|---|
| % calculated | 61.52 | 6.34 | 9.78 |
| % found | 61.71 | 6.32 | 9.67 |

EXAMPLE 84

N1-({4-[(2-Benzoylhydrazino)carbonyl]cyclohexyl}methyl)-1-(4-methoxybenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-methoxybenzenesulphonyl chloride, and in Step b replacing phenylhydrazine by phenylhydrazide.

Elemental microanalysis:

|  | C | H | N |
|---|---|---|---|
| % calculated | 59.25 | 6.06 | 9.43 |
| % found | 59.25 | 6.26 | 9.49 |

EXAMPLE 85

N1-({4-[(2-Benzoylhydrazino]carbonyl]cyclohexyl}methyl)-1-(3,4-dimethoxybenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 3,4-dimethoxybenzenesulphonyl chloride, and in Step b replacing phenylhydrazine by phenylhydrazide.

Melting point: 244–245° C.
Elemental microanalysis:

|  | C | H | N |
|---|---|---|---|
| % calculated | 57.02 | 5.99 | 8.68 |
| % found | 56.91 | 6.33 | 8.84 |

EXAMPLE 86

N1-({4-[(2-Benzoylhydrazino)carbonyl]cyclohexyl}methyl)-1-(4-acetylaminobenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 4-(N-acetylamino)benzenesulphonyl chloride, and in Step b replacing phenylhydrazine by phenylhydrazide.

Elemental microanalysis:

| | C | H | N |
|---|---|---|---|
| % calculated | 58.46 | 5.97 | 11.86 |
| % found | 58.29 | 6.04 | 11.73 |

EXAMPLE 87

N1-({4-[(2-Benzoylhydrazino)carbonyl]cyclohexyl}methyl)-1-(2-methylsulphonylbenzene)sulphonamide The expected product is obtained according to the process described in Example 40, in Step a replacing 6-aminocaproic acid by 4-(aminomethyl)cyclohexanecarboxylic acid and 2-naphthylsulphonyl chloride by 2-(methylsulphonyl)benzenesulphonyl chloride, and in Step b replacing phenylhydrazine by phenylhydrazide.

Melting point: 193–194° C.
Elemental microanalysis:

| | C | H | N |
|---|---|---|---|
| % calculated | 53.55 | 5.48 | 8.52 |
| % found | 53.17 | 5.74 | 8.49 |

EXAMPLE 88

N1-({4-[(2-Benzoylhydrazino)carbonyl]cyclohexyl}methyl)-1-(β-styrene)sulphonamide The expected product is obtained according to the process described in Example 40, in Step a replacing 6-aminocaproic acid by 4-(aminomethyl)cyclohexanecarboxylic acid and 2-naphthylsulphonyl chloride by (β-styrene)sulphonyl chloride, and in Step b replacing phenylhydrazine by phenylhydrazide.

Melting point: 208–209° C.
Elemental microanalysis:

| | C | H | N |
|---|---|---|---|
| % calculated | 60.13 | 6.32 | 9.15 |
| % found | 60.06 | 6.45 | 9.05 |

EXAMPLE 89

N1-({4-[(2-Phenylhydrazino)carbonyl]cyclohexyl}methyl)-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride.

Melting point: 218–221° C.
Elemental microanalysis:

| | C | H | N |
|---|---|---|---|
| % calculated | 54.89 | 5.84 | 10.67 |
| % found | 54.50 | 6.05 | 10.82 |

EXAMPLE 90

N1-({4-[(2-Benzoylhydrazino)carbonyl]cyclohexyl}methyl)-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride, and in Step b replacing phenylhydrazine by phenylhydrazide.

Melting point: 221–222° C.
Elemental microanalysis:

| | C | H | N |
|---|---|---|---|
| % calculated | 52.96 | 5.34 | 9.76 |
| % found | 53.14 | 5.50 | 9.82 |

EXAMPLE 91

N1-[(4-{[2-(4-Chlorophenyl)hydrazino]carbonyl}cyclohexyl)-methyl]-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride, and in Step b replacing phenylhydrazine by 4-chlorophenylhydrazine.

Melting point: 193–194° C.
Elemental microanalysis:

| | C | H | N |
|---|---|---|---|
| % calculated | 50.47 | 5.14 | 9.81 |
| % found | 50.50 | 5.27 | 9.73 |

EXAMPLE 92

N1-[(4-{[(2-(4-Chlorobenzoyl)hydrazino]carbonyl}cyclohexyl)-methyl]-1-(2-thienyl)sulphonamide The expected product is obtained according to the process described in Example 40, in Step a replacing 6-aminocaproic acid by 4-(aminomethyl)cyclohexanecarboxylic acid and 2-naphthylsulphonyl chloride by (2-thienyl)sulphonyl chloride, and in Step b replacing phenylhydrazine by 4-chlorophenylhydrazide.

Melting point: 237–239° C.
Elemental microanalysis:

-continued

|  | C | H | N |
|---|---|---|---|
| % calculated | 50.00 | 4.82 | 9.21 |
| % found | 49.93 | 4.97 | 9.37 |

EXAMPLE 93

N1-[6-Oxo-6-(2-phenylhydrazino)hexyl]-1-benzenesulphonamide

The expected product is obtained according to the process described in Example 40, replacing 2-naphthylsulphonyl chloride by benzenesulphonyl chloride.

Melting point: 123–124° C.
Elemental microanalysis:

|  | C | H | N |
|---|---|---|---|
| % calculated | 59.81 | 6.41 | 11.62 |
| % found | 59.92 | 6.58 | 11.52 |

EXAMPLE 94

N1-[6-(2-Benzoylhydrazino)-6-oxohexyl]-1-phenylsulphonamide

The expected product is obtained according to the process described in Example 40, replacing 2-naphthylsulphonyl chloride by benzenesulphonyl chloride, and phenylhydrazine by phenylhydrazide.

Melting point: 150° C.
Elemental microanalysis:

|  | C | H | N |
|---|---|---|---|
| % calculated | 58.59 | 5.95 | 10.79 |
| % found | 58.52 | 6.10 | 10.90 |

EXAMPLE 95

Benzyl N-[1-(4-methoxybenzyl)-2-oxo-2-(2-phenylsulphonyl-hydrazino)ethyl]carbamate The expected product is obtained according to the process described in Example 1, in Step a replacing phenylalanine by O-methyltyrosine, and in Step b replacing phenylhydrazine by phenylsulphonylhydrazine.

Elemental microanalysis:

|  | C | H | N |
|---|---|---|---|
| % calculated | 59.63 | 5.18 | 8.70 |
| % found | 60.03 | 5.41 | 8.65 |

EXAMPLE 96

N1-[1-(4-Methoxybenzyl)-2-oxo-2-(2-phenylsulphonylhydrazino)-ethyl]-2-phenoxyacetamide The expected product is obtained according to the process described in Example 5, in Step a replacing phenylalanine by O-methyltyrosine, and in Step b replacing phenylhydrazine by phenylsulphonylhydrazine.

Elemental microanalysis:

|  | C | H | N |
|---|---|---|---|
| % calculated | 59.63 | 5.18 | 8.70 |
| % found | 59.52 | 5.06 | 8.59 |

EXAMPLE 97

N1-[1-Benzyl-2-oxo-2-(2-phenylsulphonylhydrazino)ethyl]-1-phenylsulphonamide

The expected product is obtained according to the process described in Example 10, in Step a replacing 2-naphthylsulphonyl chloride by benzenesulphonyl chloride, and in Step b replacing phenylhydrazine by phenylsulphonylhydrazine.

Melting point: 182–183° C.
Elemental microanalysis:

|  | C | H | N |
|---|---|---|---|
| % calculated | 54.90 | 4.58 | 9.15 |
| % found | 54.70 | 4.79 | 8.91 |

EXAMPLE 98

N2-[1-Benzyl-2-oxo-2-(2-phenylsulphonylhydrazino)ethyl]-2-naphthylamide

The expected product is obtained according to the process described in Example 1, in Step a replacing benzyl chloroformate by naphthoyl chloride, and in Step b replacing phenylhydrazine by phenylsulphonylhydrazine.

Elemental microanalysis:

|  | C | H | N |
|---|---|---|---|
| % calculated | 64.41 | 4.97 | 8.35 |
| % found | 63.95 | 5.01 | 8.29 |

EXAMPLE 99

1-[(4-Chlorophenyl)sulphonyl]-N'-phenylperhydro-2-indolecarbohydrazide

The expected product is obtained according to the process described in Example 62, in Step a replacing benzenesulphonyl chloride by 4-chlorobenzenesulphonyl chloride.

Elemental microanalysis:

|  | C | H | N |
|---|---|---|---|
| % calculated | 58.13 | 5.54 | 9.68 |
| % found | 58.66 | 5.63 | 9.18 |

EXAMPLE 100

1-[(4-Chlorophenyl)sulphonyl]-N'-nicotinoyl-perhydro-2-indolecarbohydrazide

The expected product is obtained according to the process described in Example 62, in Step a replacing benzenesulphonyl chloride by 4-chlorobenzenesulphonyl chloride, and in Step b replacing phenylhydrazine by 3-pyridinecarbohydrazide.

Elemental microanalysis:

|  | C | H | N |
|---|---|---|---|
| % calculated | 54.49 | 4.97 | 12.11 |
| % found | 54.54 | 5.21 | 12.32 |

EXAMPLE 101

1-[(2-Nitrophenyl)sulphonyl]-N'-phenylperhydro-2-indolecarbohydrazide

The expected product is obtained according to the process described in Example 62, in Step a replacing benzenesulphonyl chloride by 2-nitrobenzenesulphonyl chloride.

Melting point: 86–89° C.
Elemental microanalysis:

|  | C | H | N |
|---|---|---|---|
| % calculated | 56.88 | 5.19 | 12.64 |
| % found | 56.78 | 5.49 | 12.26 |

EXAMPLE 102

N'-Benzoyl-1-[(2-nitrophenyl)sulphonyl]-perhydro-2-indolecarbohydrazide

The expected product is obtained according to the process described in Example 62, in Step a replacing benzenesulphonyl chloride by 2-nitrobenzenesulphonyl chloride, and in Step b replacing phenylhydrazine by phenylhydrazide.

Melting point: 109–113° C.
Elemental microanalysis:

|  | C | H | N |
|---|---|---|---|
| % calculated | 55.93 | 5.08 | 11.86 |
| % found | 56.21 | 5.24 | 12.05 |

EXAMPLE 103

1-[(4-Chlorophenyl)sulphonyl]-N'-phenyl-2-pyrrolidinecarbohydrazide

The expected product is obtained according to the process described in Example 62, in Step a replacing perhydroindolecarboxylic acid by proline and benzenesulphonyl chloride by 4-chlorobenzenesulphonyl chloride.

Melting point: 133–135° C.
Elemental microanalysis:

|  | C | H | N |
|---|---|---|---|
| % calculated | 53.75 | 4.74 | 11.07 |
| % found | 53.94 | 4.89 | 10.81 |

EXAMPLE 104

N'-Benzoyl-1-[(4-chlorophenyl)sulphonyl]-2-pyrrolidinecarbohydrazide

The expected product is obtained according to the process described in Example 62, in Step a replacing perhydroindolecarboxylic acid by proline and benzenesulphonyl chloride by 4-chlorobenzenesulphonyl chloride, and in Step b replacing phenylhydrazine by phenylhydrazide.

Melting point: 171–172° C.
Elemental microanalysis:

|  | C | H | N |
|---|---|---|---|
| % calculated | 53.01 | 4.42 | 10.31 |
| % found | 53.26 | 4.53 | 10.36 |

EXAMPLE 105

1-[(4-Chlorophenyl)sulphonyl]-N'-nicotinoyl-2-pyrrolidinecarbohydrazide

The expected product is obtained according to the process described in Example 62, in Step a replacing perhydroindolecarboxylic acid by proline and benzenesulphonyl chloride by 4-chlorobenzenesulphonyl chloride, and in Step b replacing phenylhydrazine by 3-pyridinecarbohydrazide.

Melting point: 107–108° C.
Elemental microanalysis:

|  | C | H | N |
|---|---|---|---|
| % calculated | 49.94 | 4.16 | 13.71 |
| % found | 50.51 | 4.40 | 13.47 |

EXAMPLE 106

1-[(4-Chlorophenyl)sulphonyl]-N'-naphthyl-2-pyrrolidinecarbohydrazide

The expected product is obtained according to the process described in Example 62, in Step a replacing perhydroindolecarboxylic acid by proline and phenylhydrazine by naphthylhydrazine.

| | C | H | N |
|---|---|---|---|
| Melting point: 178–180° C. | | | |
| Elemental microanalysis: | | | |
| % calculated | 60.80 | 4.58 | 6.76 |
| % found | 60.78 | 4.73 | 6.79 |

EXAMPLE 107

N-({4-[(2-Benzoylhydrazino)carbonyl]cyclohexyl}methyl)-5-(dimethylamino)-1-napthalenesulphonamide The expected product is obtained according to the process described in Example 40, in Step a replacing 6-aminocaproic acid by 4-(aminomethyl)cyclohexanecarboxylic acid and 2-napthylsulphonyl chloride by 5-dimethylamino-1-naphthyl sulphonyle chloride and in step b replacing phenylhydrazine by phenylhydrazide.

| | C | H | N |
|---|---|---|---|
| Melting point: 201–203° C. | | | |
| Elemental microanalysis: | | | |
| % calculated | 61.99 | 6.50 | 10.84 |
| % found | 62.81 | 6.60 | 10.83 |

EXEMPLE 108

4-Bromo-N-({4-[(2-{[4-(trifluoromethyl)-2-pyrimidinyl]carbonyl}bydrazino)carbonyl]cyclohexyl}methyl)benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by 4-bromobenzenesulphonyl chloride and in step b replacing phenylhydrazine by 4-(trifluoromethyl)-2-pyrimidinecarbohydrazide.

| | C | H | N |
|---|---|---|---|
| Melting point: 229–230° C. | | | |
| Elemental microanalysis: | | | |
| % calculated | 41.16 | 4.15 | 12.64 |
| % found | 41.06 | 4.03 | 12.75 |

EXEMPLE 109

3,4-Dimethoxy-N-[(4-{[2-(3-pyridylcarbonyl)hydrazino]carbonyl}cyclohexyl)methyl]benzenesulphonamide The expected product is obtained according to the process described in Example 40, in Step a replacing 6-aminocaproic acid by 4-(aminomethyl)cyclohexanecarboxylic acid and 2-naphthylsulphonyl chloride by 3,4-dimethoxybenzenesulphonyl chloride and in step b replacing phenylhydrazine by 3-pyridinecarbohydrazide.

| | C | H | N |
|---|---|---|---|
| Melting point: 211–212° C. | | | |
| Elemental microanalysis: | | | |
| % calculated | 55.46 | 5.88 | 11.76 |
| % found | 55.43 | 5.75 | 11.86 |

EXEMPLE 110

N-({4-[(2-Benzoylhydrazino)carbonyl]cyclohexyl}methyl)-5-quinoleinesulphonamide

The expected product is obtained according to the process described in Example 40, in Step a replacing 6-aminocaproic acid by 4-(aminomethyl)cyclohexanecarboxylic acid and 2-naphthylsulphonyl chloride by 5-quinoleinesulphonyl chloride and in step b replacing phenylhydrazine by phenylhydrazide.

| | C | H | N |
|---|---|---|---|
| Melting point: 215–216° C. | | | |
| Elemental microanalysis: | | | |
| % calculated | 61.80 | 5.58 | 12.02 |
| % found | 61.69 | 5.66 | 12.13 |

EXEMPLE 111

N-{4-[(2-Benzoylhydrazino)carbonyl]benzyl}benzenesulphonamide

The expected product is obtained according to the process described in Example 40, in Step a replacing 6-aminocaproic acid by 4-(aminomethyl)benzoic acid and 2-naphthylsulphonyl chloride by benzenesulphonyl chloride and in step b replacing phenylhydrazine by phenylhydrazide.

| | C | H | N |
|---|---|---|---|
| Melting point: 191–193° C. | | | |
| Elemental microanalysis: | | | |
| % calculated | 61.54 | 4.64 | 10.26 |
| % found | 61.57 | 4.81 | 10.22 |

EXEMPLE 112

N2-{4-[(2-Benzoylhydrazino)carbonyl]benzyl}naphthalenesulphonamide

The expected product is obtained according to the process described in Example 40, in Step a replacing 6-aminocaproic acid by 4-(aminomethyl)benzoic acid and 2-naphthylsulphonyl chloride by benzenesulphonyl chloride and in step b replacing phenylhydrazine by phenylhydrazide.

EXEMPLE 113

N-{4-[(2-Benzoylhydrazino)carbonyl]benzyl}-2-nitrobenzenesulphonamide

The expected product is obtained according to the process described in Example 40, in Step a replacing 6-aminocaproic acid by 4-(aminomethyl)benzoïc acid and 2-naphthylsulphonyl chloride by 2-nitrobenzenesulphonyl chloride and in step b replacing phenylhydrazine by phenylhydrazide.

| Elemental microanalysis: | | | |
|---|---|---|---|
| | C | H | N |
| % calculated | 55.45 | 3.96 | 12.32 |
| % found | 55.36 | 4.11 | 12.56 |

EXEMPLE 114

N-{4-[(2-Benzoylhydrazino)carbonyl]benzyl}4-bromobenzenesulphonamide

The expected product is obtained according to the process described in Example 40, in Step a replacing 6-aminocaproic acid by 4-(aminomethyl)benzoïc acid and 2-naphthylsulphonyl chloride by 2-bromobenzenesulphonyl chloride and in step b replacing phenylhydrazine by phenylhydrazide.

Melting point: 208–210° C.

| Elemental microanalysis: | | | |
|---|---|---|---|
| | C | H | N |
| % calculated | 50.71 | 3.82 | 8.45 |
| % found | 50.85 | 3.61 | 8.42 |

PHARMACOLOGICAL STUDY

EXAMPLE A

Measurement of the in vitro affinity for NPY receptors

The capacity of the compounds of the invention to bind to NPY receptors was measured on various cell lines, each expressing one of the receptor sub-types studied. Competition binding experiments were carried out using the peptide [$^{125}$I]-PYY as radioligand at concentrations ranging from 15 to 65 pM. The non-specific fraction is measured in the presence of a concentration of 1 μM NPY. The cells are incubated for a period ranging from 1 to 2 hours depending upon the lines, and the radioactivity is collected after filtration over a GF/C filter treated with 0.1% PEI, before being measured.

Results:

The results are expressed as $IC_{50}$. The compounds of the invention appear to be capable of significantly displacing the reference ligand: the $IC_{50}$ values vary from a few nanomoles to some hundreds of nanomoles.

By way of example, the compound of Example 44 has an $IC_{50}$ of 14.5 nM for the $Y_5$ receptor.

EXAMPLE B

Measurement of the effect on food intake and weight development in the obese mouse The compounds of the invention were administered in vivo to the obese ob/ob mouse in order to evaluate their influence on food intake and weight development. The animals used are 13- to 18-week-old female ob/ob C57B1/6J mice. They are divided into groups each comprising 4 animals per cage, the cages being fitted with a grating floor, and the mice having free access to food.

Before the experiments, the animals are conditioned for a period ranging from 2 to 3 weeks until their food consumption has stabilised. The experiments may be summarised as follows:
D −14 to D −7: conditioning
D −7 to D −3: measurement of the basal food intake
D0 to D +3: animals treated twice daily, the control groups being given the carrier
D0 to D +4: daily measurement of food intake and body weight The test products are dissolved, immediately before use, in water, 0.9% sodium chloride, propylene glycol or dimethyl sulphoxide, depending upon their solubility, and are administered intraperitoneally (IP), in a volume of 2.5 ml/kg.

The parameters measured are the weight of the feed troughs containing the food and the body weight.

Results:

The results are expressed as:
percentage variation in food intake under treatment compared with the basal food intake;
percentage variation in body weight between the first and last day of treatment.

By way of example, the results obtained with the compound of Example 44 are as follows:

| Product | Dose (mg/kg) | Food intake % variation (D1) | | Body weight % variation (D4/D0) |
|---|---|---|---|---|
| | | Control | Treated | |
| Example 44 | 5 | −25.3 | −75.2 | −6.0 |

EXAMPLE C

Acute toxicity study

The acute toxicity was evaluated after oral administration of increasing doses of the test compound to groups each comprising 8 mice (26±6 gramms). The animals were observed at regular intervals over the course of the first day and daily for the two weeks following treatment.

The compounds of the invention appear to be not very toxic at all.

EXAMPLE D

Pharmaceutical composition

Formulation for the preparation of 1000 tablets each comprising a dose of 10 mg

| | |
|---|---|
| Compound of Example 44 | 10 g |
| Hydroxypropyl cellulose | 2 g |
| Wheatstarch | 10 g |
| Lactose | 100 g |
| Magnesium stearate | 3 g |
| Talc | 3 g |

We claim:

1. A compound selected from those of formula (I):

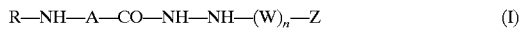

R—NH—A—CO—NH—NH—(W)$_n$—Z    (I)

wherein:

n is 0 or 1,

W represents —CO— or S(O)$_r$ wherein r is 0, 1 or 2,

Z represents a group selected from optionally substituted aryl, optionally substituted arylalkyl, optionally substituted heteroaryl and optionally substituted heteroarylalkyl, R represents a group selected from:
$Z_1$—T—CO—
$Z_1$—O—T—CO—
$Z_1$—T—O—CO—
$Z_1$—T—S (O)$_q$— wherein:

$Z_1$ represents optionally substituted aryl, optionally substituted arylalkyl, optionally substituted heteroaryl, or optionally substituted heteroarylalkyl, T represents a σ bond, alkylene, alkenylene, or alkynylene, q represents 0, 1 or 2, when n=1

A represents linear or branched alkylene having 3 to 8 carbon atoms, linear or branched alkenylene having 3 to 8 carbon atoms, linear or branched alkynylene having 3 to 8 carbon atoms, alkylenecycloalkylene, cycloalkylenealkylene, alkylenecycloalkylene, alkylenearylene, arylenealkylene, alkylenearylenealkylene,

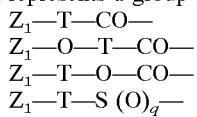

—CH—
|
B$_1$ wherein B$_1$ represents optionally substituted aryl, optionally substituted arylalkyl, optionally substituted heteroaryl, or optionally substituted heteroarylalkyl, or A forms with the nitrogen atom a grouping

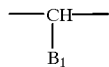

when n=0

A represents linear or branched alkenylene having 3 to 8 carbon atoms, linear or branched alkynylene having 3 to 8 carbon atoms, alkylenecycloalkylene, cycloalkylenealkylene, alkylenecycloalkylene, alkylenearylene, arylenealkylene, alkylenearylenealkylene,

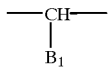

—CH—
|
B$_1$ wherein B$_1$ represents optionally substituted aryl, optionally substituted arylalkyl, optionally substituted heteroaryl, or optionally substituted heteroarylalkyl, or A forms with the nitrogen atom a grouping

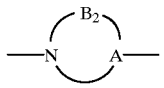

wherein B$_2$ represents saturated or unsaturated mono- or bicyclic system having 5 to 11 ring members, optionally containing 1 to 3 additional hetero atoms selected from nitrogen, oxygen and sulphur, with the proviso that when simultaneously n is 0, A represents

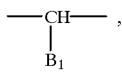

—CH—  ,
|
B$_1$

B$_1$ being benzyl, and Z represents optionally substituted phenyl, then R is other than benzoyl, at least one of R, Z, and A being or containing a heterocycle, heteroaryl, or heteroarylalkyl, their enantiomers, diastereoisomers, and addition salts thereof with a pharmaceutically-acceptable acid or base, it being understood that:

at least one of R, Z, and A being or containing a heterocycle, heteroaryl, or heteroarylalkyl, the term "alkyl" denotes a linear or branched group having 1 to 6 carbon atoms, the term "alkylenene" denotes a linear or branched bivalent radical containing 1 to 6 carbon atoms, unless indicated otherwise, the term "alkenylene" denotes a linear or branched bivalent radical containing from 2 to 6 carbon atoms and 1 to 3 double bonds, unless indicated otherwise, the term 'alkynylene" denotes a linear or branched bivalent radical containing 2 to 6 carbon atoms and 1 to 3 triple bonds, unless indicated otherwise, the term "aryl" denotes phenyl, naphthyl, dihydronaphthyl or tetrahydronaphthyl, and the term "arylene" denotes a bivalent radical of the same type, the term "heteroaryl" denotes an unsaturated or partially unsaturated mono- or bi-cyclic group having 5 to 11 ring members, containing 1 to 4 hetero atoms selected from nitrogen, oxygen, and sulphur, the term "alkylenecycloalkylene" represents —A$_1$—A$_2$—, the term "cycloalkylene-alkylene" represents —A$_2$—A$_1$—, and the term "alkylenecycloalkylene-alkylene" represents —A$_1$—A$_2$—A$_1$, the term "alkylenearylene" represents —A$_1$—A$_3$—, the term "arylenealkylene" represents —A$_3$—A$_1$—, the term "alkylenearylenealkylene" represents —A$_1$—A$_3$—A$_1$—, wherein A$_1$ is alkylene as defined hereinbefore, A$_2$ is (C$_4$–C$_8$)cycloalkylene, and A$_3$ is arylene as defined hereinbefore, the expression "optionally substituted" applied to the terms "aryl", "arylalkyl", "heteroaryl" and "heteroarylalkyl" indicates that those groups are substituted on their cyclic moiety by 1 to 5 identical or different substituents selected from linear or branched ($C_1$–$C_6$) alkyl, linear or branched ($C_1$–$C_6$)alkoxy, halogen, hydroxy, perhalo-($C_1$–$C_6$)alkyl in which the alkyl moiety is linear or branched, nitro, linear or branched ($C_1$–$C_6$)acyl, linear or branched ($C_1$–$C_6$) alkylsulphonyl, and amino (amino optionally being substituted by one or two linear or branched ($C_1$–$C_6$) alkyl and/or linear or branched ($C_1$–$C_6$)acyl).

2. A compound of claim 1 wherein W represents —CO—.

3. A compound of claim 1 wherein W represents —$SO_2$—.

4. A compound of claim 1 wherein R represents $Z_1$—T—CO, T being alkylene or a bond.

5. A compound of claim 1 wherein R represents $Z_1$—O—T—CO.

6. A compound of claim 1 wherein R represents $Z_1$—T—O—CO.

7. A compound of claim 1 wherein R represents $Z_1$—T—S(O)$_q$—, T being alkylene or a bond.

8. A compound of claim 1 wherein Z represents an optionally substituted aryl or optionally substituted heteroaryl.

9. A compound of claim 1 wherein A represents

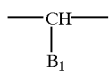

wherein $B_1$ is optionally substituted arylalkyl.

10. A compound of claim 1 wherein A represents alkylenecycloalkylene.

11. A compound of claim 1 wherein A represents alkylenearylene.

12. A compound of claim 1 wherein A represents

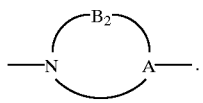

13. A compound of claim 1 selected from those wherein W represents —CO—, Z represents a group selected from optionally substituted aryl and optionally substituted heteroaryl, R represents a grouping selected from $Z_1$—T—CO—, $Z_1$—O—T—CO—, $Z_1$—T—O—CO— and $Z_1$—T—S(O)$_q$— wherein $Z_1$ is optionally substituted aryl or optionally substituted heteroaryl, T represents alkylene, and q is 2, and A represents alkylenecycloalkylene,

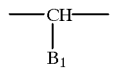

wherein $B_1$ is optionally substituted arylalkyl, or A forms with the adjacent nitrogen atom a pyrrolidine, perhydroindole, or piperidine group, and its enantiomers, diastereoisomers, and addition salts thereof with a pharmaceutically-acceptable acid or base.

14. A compound of claim 1 which is selected from N1-[(4-{[2-(2-indolylcarbonyl)hydrazino]carbonyl}cyclohexyl)methyl]-1l-(2-nitrobenzene) sulphonamide and its enantiomers, diastereoisomers, and addition salts thereof with a pharmaceutically-acceptable acid or base.

15. A compound of claim 1 which is selected from N1-({4-[(2-benzylhydrazino)carbonyl]cyclohexyl}methyl)-1-(2-thienyl)sulphonamide, and its enantiomers, diastereoisomers, and addition salts thereof with a pharmaceutically-acceptable acid or base.

16. A pharmaceutical composition useful as Neuropeptide Y receptor ligand comprising as active principle an effective amount of a compound as claimed in claim 1, together with with one or more pharmaceutically-acceptable excipients or vehicles.

17. A method for treating an animal or living body afflicted with a condition requiring a neuropeptide Y receptor ligand and associated with eating behaviour disorders and/or energy balance disorders selected from diabetes, obesity, bulimia, and anorexia nervosa, comprising the step of administering to the living body an amount of a compound of claim 1 which is effective for alleviation of said condition.

18. A method for treating an animal or living body afflicted with a condition requiring a neuropeptide Y receptor ligand selected from arterial hypertension, anxiety, depression, epilepsy, sexual dysfunctions and sleep disorders, comprising the step of administering to the living body an amount of a compound of claim 1 which is effective for alleviation of said condition.

* * * * *

UNITED STATES PATENT AND TRADEMARK OFFICE
CERTIFICATE OF CORRECTION

PATENT NO. : 6,271,247 B1
DATED : August 7, 2001
INVENTOR(S) : Antonio Monge Vega et al.

It is certified that error appears in the above-identified patent and that said Letters Patent is hereby corrected as shown below:

<u>Column 44,</u>
Line 33, please delete line.
Line 34, please delete "heterocycle, heteroaryl, or heteroarylalkyl"

<u>Column 46,</u>
Line 18, "11" should read -- 1 --

Signed and Sealed this

Eleventh Day of December, 2001

Attest:

NICHOLAS P. GODICI
*Attesting Officer*     *Acting Director of the United States Patent and Trademark Office*